United States Patent [19]
Grabenkort

[11] Patent Number: 5,785,682
[45] Date of Patent: Jul. 28, 1998

[54] PRE-FILLED SYRINGE DRUG DELIVERY SYSTEM

[75] Inventor: Richard E. Grabenkort, Barrington, Ill.

[73] Assignee: Abbott Laboratories, Abbott Park, Ill.

[21] Appl. No.: 616,798

[22] Filed: Mar. 15, 1996

Related U.S. Application Data

[63] Continuation-in-part of Ser. No. 408,436, Mar. 22, 1995, abandoned.

[51] Int. Cl.⁶ .................................................. A61M 37/00
[52] U.S. Cl. ................................ 604/82; 604/85; 604/191
[58] Field of Search ........................... 604/82, 19, 27, 604/36, 38, 51, 56, 60, 83, 84, 85, 86, 87, 88, 92, 181, 187, 191, 200, 201, 203, 218, 232, 234; 128/919

[56] References Cited

U.S. PATENT DOCUMENTS

| | | |
|---|---|---|
| 2,475,939 | 7/1949 | Applezweig. |
| 3,477,432 | 11/1969 | Shaw. |
| 3,489,147 | 1/1970 | Show. |
| 3,754,644 | 8/1973 | Hempel. |
| 3,757,779 | 9/1973 | Rovinski. |
| 4,153,057 | 5/1979 | Kobel. |
| 4,172,457 | 10/1979 | Choksi et al.. |
| 4,243,080 | 1/1981 | Choksi et al.. |
| 4,581,016 | 4/1986 | Gettig. |
| 4,840,616 | 6/1989 | Banks. |
| 4,957,637 | 9/1990 | Cornell. |
| 5,067,998 | 11/1991 | Singh et al.. |
| 5,088,996 | 2/1992 | Kopfer et al.. |
| 5,125,892 | 6/1992 | Drudik. |
| 5,135,507 | 8/1992 | Haber et al.. |
| 5,158,546 | 10/1992 | Haber et al.. |
| 5,176,639 | 1/1993 | Pozzi et al.. |
| 5,181,909 | 1/1993 | McFarlane .................. 604/191 X |
| 5,289,858 | 3/1994 | Grabenkort. |
| 5,298,024 | 3/1994 | Richmond. |
| 5,372,586 | 12/1994 | Haber et al.. |
| 5,407,431 | 4/1995 | Botich et al.. |
| 5,472,431 | 12/1995 | Godat et al.. |
| 5,496,288 | 3/1996 | Sweeney. |
| 5,520,657 | 5/1996 | Sellers et al.. |
| 5,569,193 | 10/1996 | Hofsetter et al.. |

FOREIGN PATENT DOCUMENTS

| | | |
|---|---|---|
| 0302248 A1 | 2/1989 | European Pat. Off.. |
| 0599649 A1 | 6/1994 | European Pat. Off.. |
| 0695555 A1 | 2/1996 | European Pat. Off.. |
| WO 9201485 | 2/1992 | WIPO. |

*Primary Examiner*—Wynn Wood Coggins
*Assistant Examiner*—N. Kent Gring
*Attorney, Agent, or Firm*—Neal D. Marcus

[57] ABSTRACT

A drug delivery system includes first drug (110) and second diluent (182) syringe assemblies which are respectively pre-filled with a drug concentrate and a liquid diluent. The diluent syringe assembly is positionable in operative association within a sterility maintenance sleeve (150) of the first syringe assembly so that the assemblies are joined in fluid communication. This fluid transfer connection permits the diluent to be transferred from the second syringe assembly into a sterile mixing chamber defined by a reciprocable stopper (134) in the first syringe assembly. Thereafter, the second syringe assembly can be moved with respect to the barrel of the first syringe assembly so that the resulting mixture can be delivered for patient administration.

15 Claims, 7 Drawing Sheets

PRE-FILLED SYRINGE DRUG DELIVERY SYSTEM

This is a continuation-in-part application of U.S.A. patent application Ser. No. 08/408,436, filed on Mar. 22, 1995 abandoned.

TECHNICAL FIELD

The present invention relates generally to medical devices for the preparation and administration of drugs and other therapeutic solutions, and more particularly to a drug delivery system which includes first and second syringe assemblies which are pre-filled with a drug and a liquid diluent, respectively. The syringe assemblies are positionable in a generally telescopic relationship with each other for mixing the drug with the diluent, and thereafter administering the resultant mixture to a patient.

BACKGROUND OF THE INVENTION

Modern healthcare facilities typically require the preparation and administration to patients of a very large number of pharmaceutical solutions such as intravenous drug solutions and other medicaments. In some instances, premixed solutions are provided to the healthcare facility, with subsequent administration to the patient in this ready to use form.

However, some drug compositions are supplied in a concentrated form, which may be either liquid or particulate in nature. Preparation of the solution for administration to the patient may require mixing, either for dilution or reconstitution, with a sterile liquid, such as sterile water or saline. Efficient storage and handling of such concentrated compositions is facilitated since the drugs are not as bulky as they would be if supplied in the diluted concentration (i.e. premixed or ready to use).

The drug delivery system of the present invention has been particularly configured to facilitate efficient and convenient preparation and administration of drug solutions and other wet or dry medicaments. Pre-filled syringe assemblies are provided which are conveniently operable to dilute a concentrated drug composition or to reconstitute a drug in dry form, and thereafter to administer the resultant solution.

SUMMARY OF THE INVENTION

The syringe drug delivery system of the present invention includes first and second pre-filled syringe assemblies which are positionable in a generally telescopic relationship with each other for effecting preparation of a drug-containing solution, and subsequent administration of the same. This is achieved by providing a first syringe assembly with a selected quantity of a concentrated drug or other medicament, which may be in dry, particulate form, or in the form of a liquid concentrate. The second syringe assembly can be pre-filled, or filled just prior to use, with a liquid diluent or the like, such as a sterile saline solution. The syringe assemblies are positioned in operative association with each other so that the liquid diluent can be mixed with the drug concentrate, and the resultant mixture thereafter administered from the assembled first and second syringes. The entire system is preferably configured for single use, so that the entire arrangement can thereafter be disposed of economically.

In one embodiment of the invention, the drug delivery system includes a first syringe assembly including a first syringe barrel having an open end and an opposite, delivery

2 end which defines a drug delivery passage. The first syringe assembly further includes a reciprocable stopper internally positioned within the first syringe barrel in slidably sealing engagement therewith. The reciprocable stopper defines an expandable, internal mixing chamber within the first syringe barrel. The mixing chamber is in fluid communication with the delivery passage.

A sterility maintenance sleeve extends from the reciprocable stopper toward the open end of the barrel of the first syringe assembly. The sterility maintenance sleeve maintains the sterility of the inside surface of the first syringe barrel while accommodating movement of the reciprocable stopper outwardly and then inwardly within the first syringe barrel.

The delivery system further includes a second syringe assembly including a second syringe barrel having a fluid discharge passage at one end thereof. A movable piston plunger is positionable within the second syringe barrel to define a fluid chamber therein. The fluid chamber is in fluid communication with the fluid discharge passage. The first syringe assembly is preferably pre-filled with a drug concentrate, which is sealed within the internal mixing chamber. The second syringe assembly can be pre-filled with a liquid diluent held in the fluid chamber.

In order to mix the drug concentrate and the liquid diluent provided in the first and second syringe assemblies, the drug delivery system of the present invention includes a fluid transfer connector means or coupling means for joining the fluid chamber of the second syringe assembly in fluid communication with the internal mixing chamber of the first syringe assembly. Such fluid communication is achieved when the second syringe assembly is positioned, in a generally telescopic relationship with the first syringe assembly, so that the second syringe assembly is directly or indirectly connected with, or in engagement with, the reciprocable stopper of the first syringe assembly.

In one form of the invention, the connector arrangement includes a cannula which is mounted on the second syringe assembly and which is insertable through the reciprocable stopper of the first syringe assembly as the first and second syringe assemblies are telescopically joined. Further, the reciprocable stopper of the first syringe assembly and the syringe barrel of the second syringe assembly respectively include threaded connecting means for threadably connecting the second syringe barrel to the reciprocable stopper. As the second syringe barrel and the reciprocable stopper are threadably connected, the cannula mounted on the second syringe assembly is being inserted through the reciprocable stopper.

In another embodiment, the reciprocable stopper is elastomeric and hollow and includes a slit valve having flaps or lips normally biased closed. The reciprocable stopper has a receiving cavity for receiving the enlarged head of the sterility maintenance sleeve. The sterility maintenance sleeve is also connectable to the syringe barrel of the second syringe assembly. The sterility maintenance sleeve also has an outlet passage establishing fluid communication between the diluent in the second syringe assembly barrel and the slit valve of the reciprocable stopper.

With either embodiment, once the first and second syringe assemblies are operatively connected, the liquid diluent within the fluid chamber of the second syringe assembly can be caused to flow into the internal mixing chamber of the first syringe assembly by movement of the piston plunger of the second syringe assembly within the syringe barrel of the second syringe assembly. During this action, hydraulic pressure expands the expandable internal mixing chamber of the first syringe assembly by moving the reciprocable stopper toward the open end of the first syringe barrel. The drug concentrate in the mixing chamber is thereby mixed with the diluent flowing from the second syringe assembly.

After mixing is complete, the resultant mixture is caused to flow from the mixing chamber by movement of the second syringe assembly together with the reciprocable stopper and sterility maintenance sleeve inwardly in the first syringe barrel of the first syringe assembly. The resultant mixture flows out of the first syringe assembly through the delivery passage which is in fluid communication with the internal mixing chamber. The delivery passage can be connected to a suitable connector or tubing or the like for administration of the drug mixture to a patient.

Other features and advantages of the present drug delivery system will become readily apparent from the following detailed description, the accompanying drawings, and the appended claims.

DETAILED DESCRIPTION

While the present invention is susceptible of embodiment in various forms, there are shown in the drawings and there will hereinafter be described only some embodiments, with the understanding that the present disclosure is to be considered as an exemplification of the invention, and is not intended to limit the invention to the specific embodiments illustrated.

Figure 1:
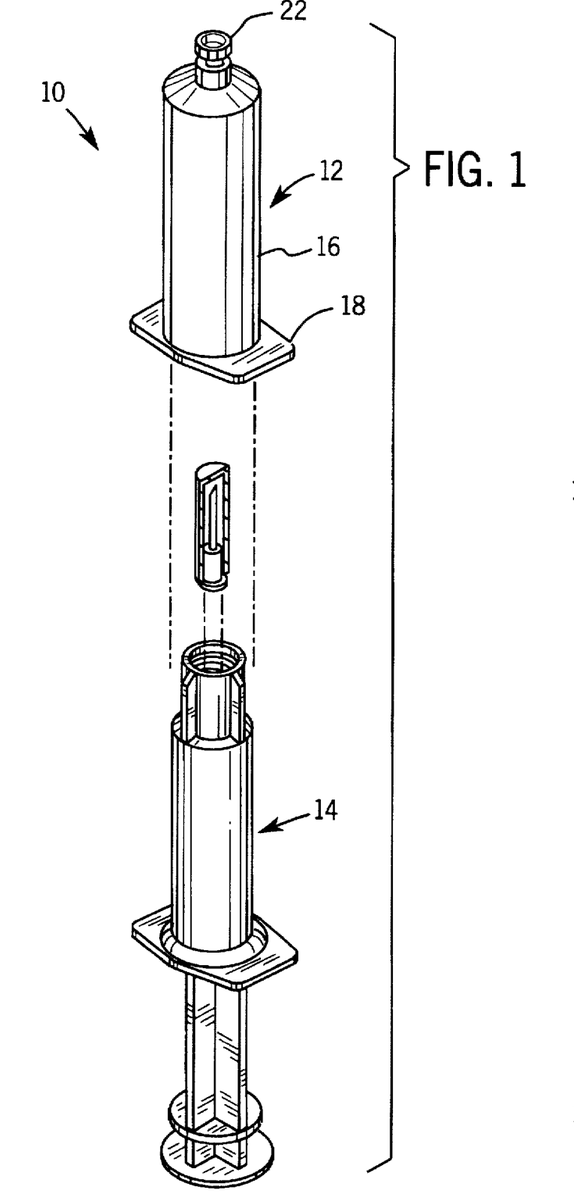
FIG. 1 is an exploded perspective view illustrating the drug delivery system embodying the principles of a first embodiment of the present invention.
Figure 2:
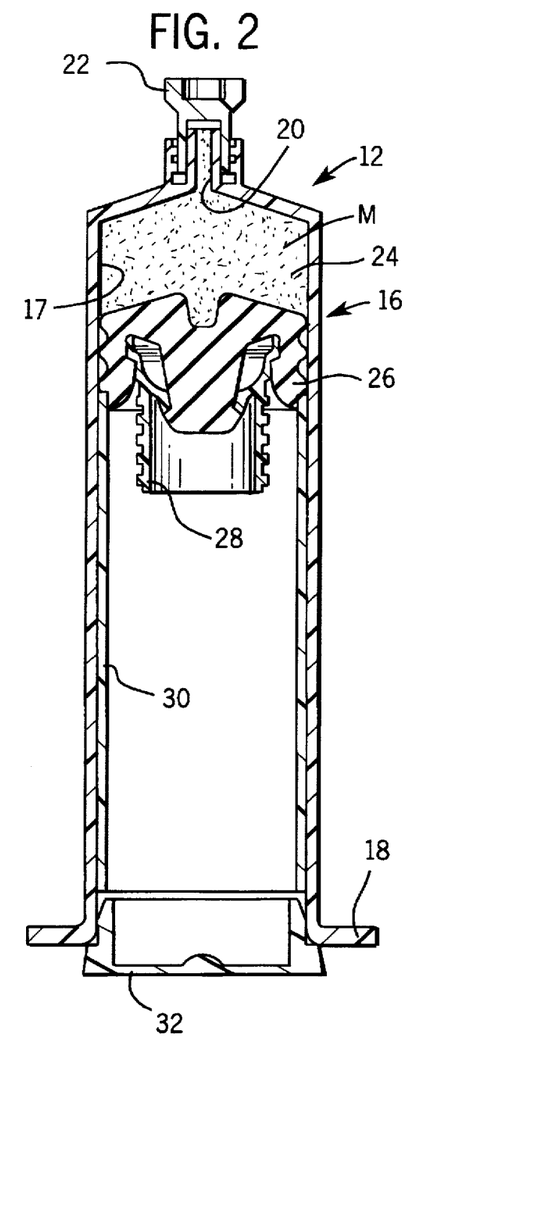
FIG. 2 is a cross-sectional view of a first syringe assembly of the first embodiment, which assembly is pre-filled with a drug concentrate designated M.
Figures 3, 4:
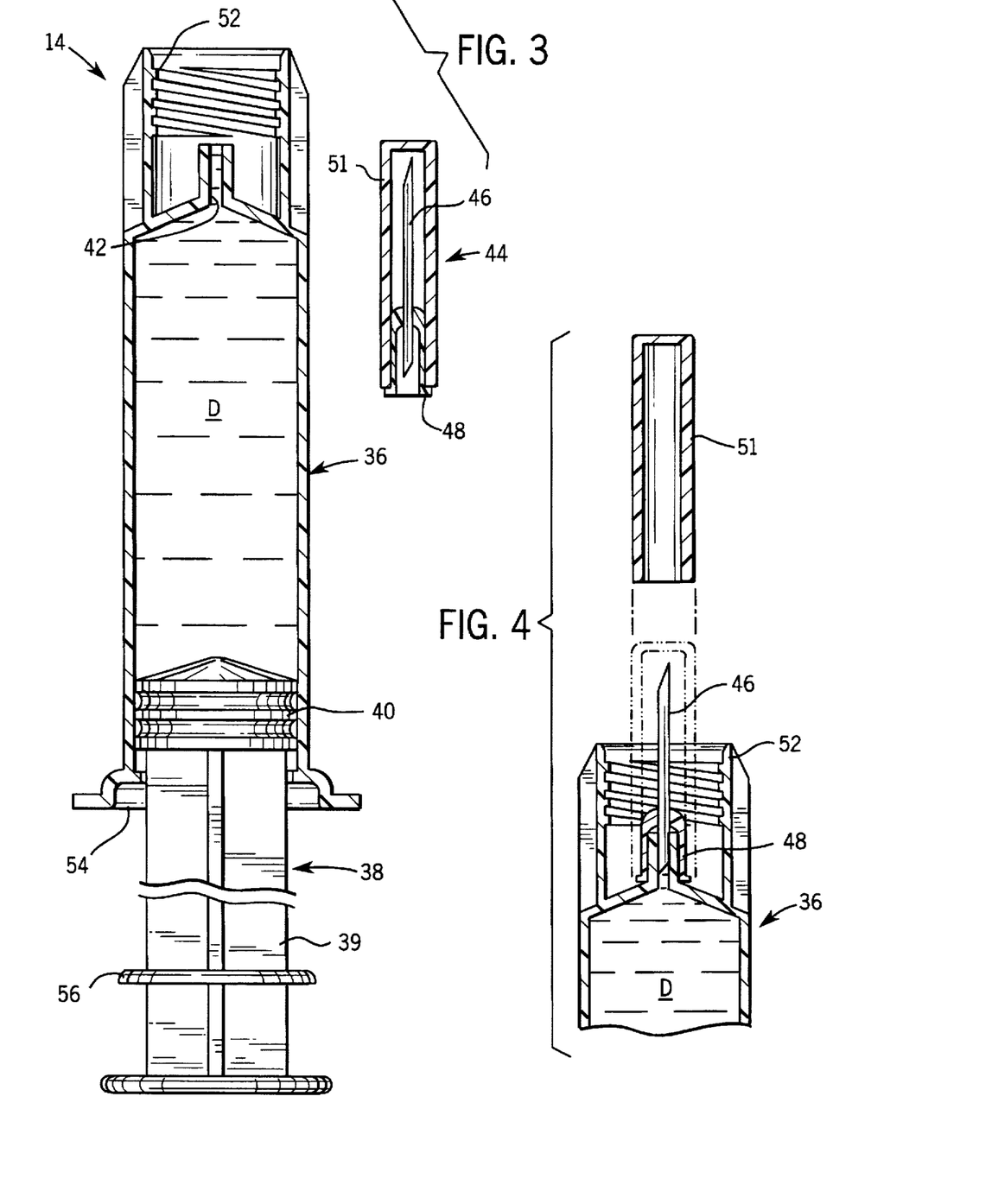
FIG. 3 is a cross-sectional view illustrating a second syringe assembly of the first embodiment, which second syringe assembly is pre-filled with a liquid diluent D.
FIG. 4 is a cross-sectional, fragmentary view of the second syringe assembly.

With reference first to FIGS. 1–3, therein is illustrated a first embodiment of a drug delivery system 10 embodying the principles of the present invention. As will be further described, the present system includes a first syringe assembly, generally designated 12, which is pre-filled with a first constituent, such as a drug concentrate or other medicament, illustrated in particulate form and generally designated M (see FIG. 2). The present system further includes a second syringe assembly, generally designated 14, which is positionable generally telescopically within the first syringe assembly 12 for effecting mixture of a second constituent, such as a liquid diluent D (FIG. 3) provided in the second syringe assembly 14 with the medicament M in the first syringe assembly.

With particular reference to FIG. 2, the first syringe assembly 12 includes a generally cylindrical first syringe barrel 16 having a cylindrical interior surface 17 and a transverse flange portion 18 at a generally open end of the barrel. The barrel 16 has a generally closed end at which a drug delivery passage 20 is defined. A removable cap or closure 22 is preferably provided to close and seal the drug delivery passage 20 prior to use of the present system.

The first syringe assembly 12 further includes an internally reciprocable stopper 26, preferably elastomeric and slidably and sealingly positioned within the interior surface of the first syringe barrel 16. The reciprocable stopper 26 defines, with the interior surface of the first syringe barrel 16, an internal mixing chamber 24 within which a drug or other medicament M is provided in either dry or liquid concentrate form. The reciprocable stopper 26 may be alternatively described as a grommet, slidable seal, or slidable piston, and these terms may be used interchangeably.

In the first embodiment illustrated in FIGS. 1–8, the reciprocable stopper 26 is provided with a thread form or threaded sleeve portion 28 which facilitates connection of the reciprocable stopper 26 with the associated second syringe assembly 14, as will be further described. The reciprocable stopper 26 is movable or reciprocable within the first syringe barrel 16 so that the internal mixing chamber 24 can expand to accommodate mixing of the liquid diluent D from the second syringe assembly with the medicament M in the first syringe assembly. A movable sleeve is therefore provided for maintaining the sterility of the interior surface 17 of the first syringe barrel 16. The sterility maintenance sleeve 30 is preferably connected to the reciprocable stopper 26, with the sterility maintenance sleeve 30 extending from the reciprocable stopper 26 generally toward the open end of the barrel 16. The sterility maintenance sleeve 30 further desirably acts to support and position the reciprocable stopper 26 within the barrel 16. A removable cap 32 is provided to close and seal the interior of the sterility maintenance sleeve 30, the threaded sleeve portion 28, and the exposed portion of reciprocable stopper 26 prior to use.

The second syringe assembly 14 includes a second syringe barrel 36 having an outside diameter that is less than the inside diameter of the sterility maintenance sleeve 30 of the first syringe assembly 12 so that the entire second syringe assembly 14 can be inserted in telescopic fashion into the sterility maintenance sleeve 30 of the first syringe assembly 12. As best illustrated in FIG. 3, the second syringe assembly 14 is of a generally conventional configuration, including a barrel 36 and a movable piston plunger or plunger assembly 38 having a plunger stem 39 and an elastomeric piston portion 40. The piston portion 40 is slidably positionable and sealingly engages the interior surface of the second syringe barrel 36. The plunger stem 39 of the piston plunger 38 extends generally from an open end of the second syringe barrel 36. The opposite end of the second syringe barrel 36 is generally closed to define a fluid discharge passage 42. The second syringe barrel 36 and the piston portion 40 of the movable piston plunger 38 together define an internal fluid chamber in the second syringe assembly 14. The fluid chamber is in fluid communication with the fluid passage 42.

As noted, use of the present system includes mixing of a liquid diluent D from the internal fluid chamber of the second syringe assembly 14 with the drug concentrate M held in the internal mixing chamber 24 of the first syringe assembly 12. Accordingly, the chambers of the respective syringe assemblies must be joined in fluid communication, and to this end, the second syringe assembly 14 includes a cannula assembly 44 which is preferably mounted on the second syringe assembly 14 (see FIG. 4). The cannula assembly 44 includes a cannula 46 which is mounted on the substantially closed end of second syringe barrel 36 by a cannula mounting element 48 so that the cannula 46 is joined in fluid communication with discharge passage 42. A removable cover 51 can cover the cannula.

In a preferred embodiment (with reference to FIGS. 5–7), a collapsible sheath 50 is provided for enclosing the cannula 46 prior to use of the present system. As will be further described, the collapsible sheath 50 includes a penetrable end wall portion, which is penetrated by the cannula 46 during use. Sheath 50 also includes a collapsible side wall portion depending from the end wall, which side wall portion collapses as the second syringe assembly 14 is operatively connected with the first syringe assembly 12, and the cannula 46 penetrates the end wall of the sheath 50. The end wall portion may also be partially or completely pre-slit to facilitate penetration by a modified cannula 46A, which can be provided as a blunt (i.e., non-sharpened) cannula.

The reciprocable stopper 26 of the first syringe assembly 12 and the syringe barrel 36 of the second syringe assembly 14 are respectively provided with a threaded connector arrangement so that these components can be threadably connected attendant to disposition of the second syringe assembly 14 within the first syringe assembly 12. As noted, threaded sleeve portion 28 preferably extends from the reciprocable stopper 26. A threaded collar portion 52, having a thread form or threads configured for mating engagement with the threads of the threaded sleeve portion 28, is provided, either integrally or as an attached piece, on the outer end of the second syringe barrel 36 of the second syringe assembly 14.

While the second syringe assembly 14 is, in many respects, generally conventional in configuration, the second syringe assembly 14 is preferably provided with an arrangement for locking the movable piston plunger 38 generally at its innermost disposition with respect to the second syringe barrel 36. In the illustrated embodiment, this locking arrangement comprises a locking recess 54 positioned generally at the open end of the second syringe barrel 36. The locking recess 54 is configured (such as with a snap-fit receiving groove) to receive and retain a cooperating locking flange 56 provided on the plunger stem 39 of the movable piston plunger 38. As will be further described, the provision of the locking recess 54 and locking flange 56 permits the forward movement of the movable piston plunger 38 in the second syringe barrel 36, and thereafter facilitates movement of the second syringe barrel 36 and piston plunger 38 (while locked or snapped together) in unison relative to the first syringe barrel 16 of first syringe assembly 12.

Figure 5:
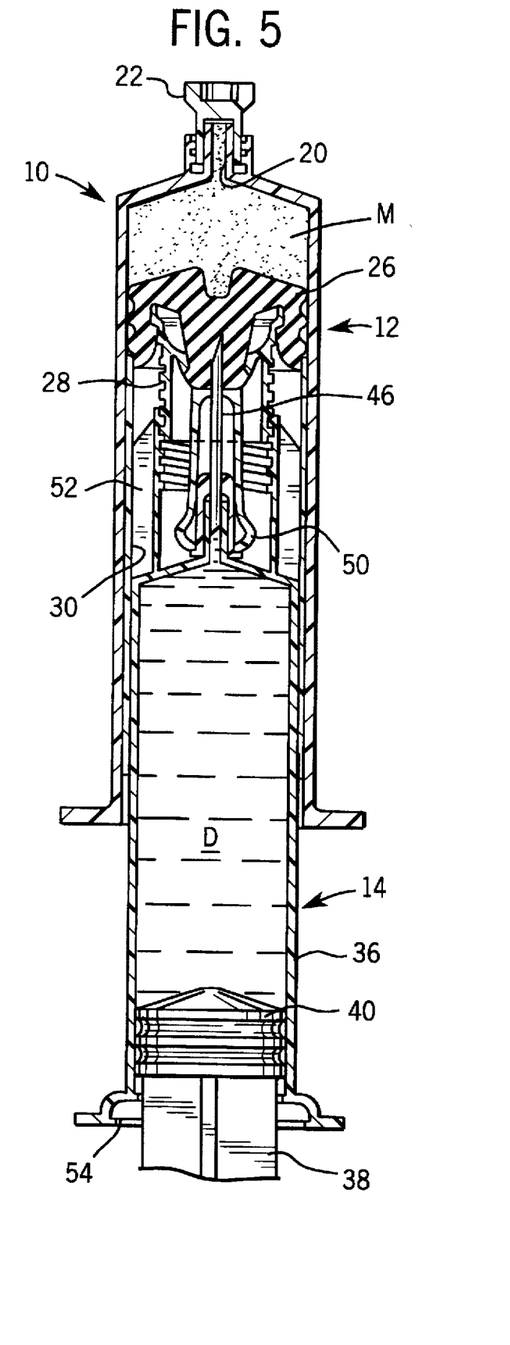
FIGS. 5 and 6 are cross-sectional views of the first embodiment and illustrate insertion of the second syringe assembly telescopically into the first syringe assembly.
Figure 6:
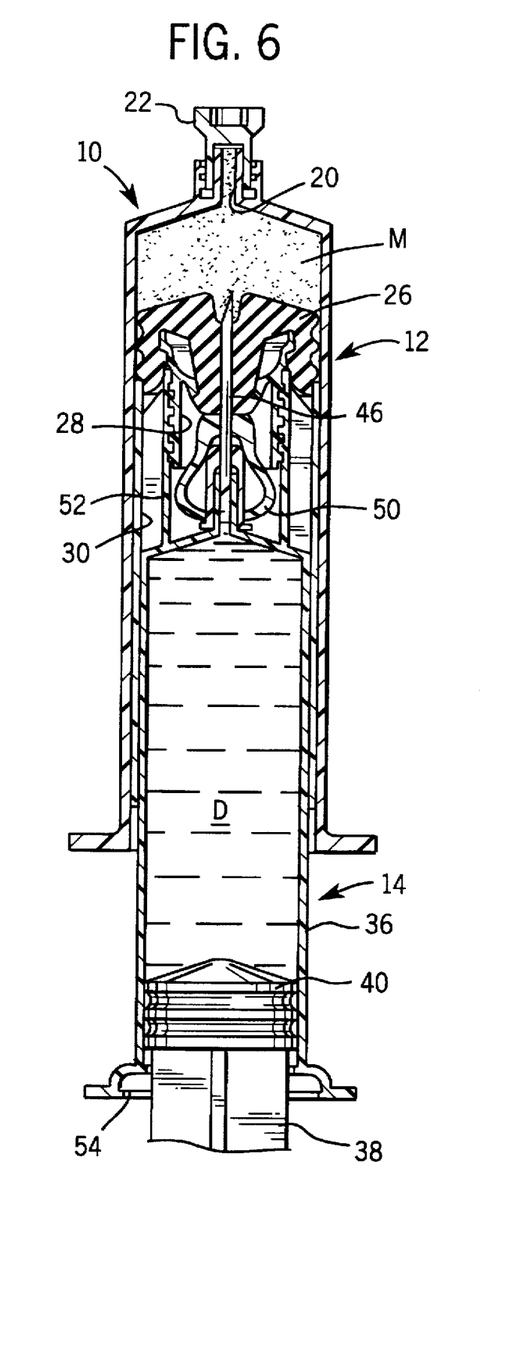

With particular reference now to FIGS. 5 and 6, use of the present system will now be described. Prior to telescopic disposition of second syringe assembly 14 generally within first syringe assembly 12, the second syringe assembly is pre-filled with liquid diluent D. The end cap 32 of the first syringe assembly 12 is then removed. Thereafter, the second syringe assembly 14 is inserted into the first syringe assembly 12, and rotated so that the threaded collar portion 52 is threadably connected to threaded sleeve portion 28. As the collar portion 52 of the second syringe barrel 36 is thus threadably joined to the threaded sleeve portion 28 of reciprocable stopper 26, collapsible sheath 50 surrounding cannula 46 is collapsed by engagement with reciprocable stopper 26. The cannula 46 thus penetrates the end wall of the collapsible sheath 50, and thereafter pierces the reciprocable stopper 26. During assembly of the first and second syringes, the reciprocable stopper 26 remains generally fixed with respect to the first syringe barrel 16, while the elastomeric piston portion 40 of the second syringe assembly remains generally fixed with respect to second syringe barrel 36.

As the threaded collar portion 52 is rotated and threadably engaged with the threaded sleeve portion 28, the cannula 46 penetrates reciprocable stopper 26. As the cannula 46 is inserted through the reciprocable stopper 26, the internal mixing chamber 24 of the first syringe assembly 12 is joined in fluid communication with the internal fluid chamber of the second syringe assembly 14. The assembled configuration of the components of the drug delivery system is illustrated in FIG. 6. The system is now ready for mixing of liquid diluent D with drug concentrate M by movement of the movable piston plunger 38 inwardly in the second syringe barrel 36.

Figure 7:
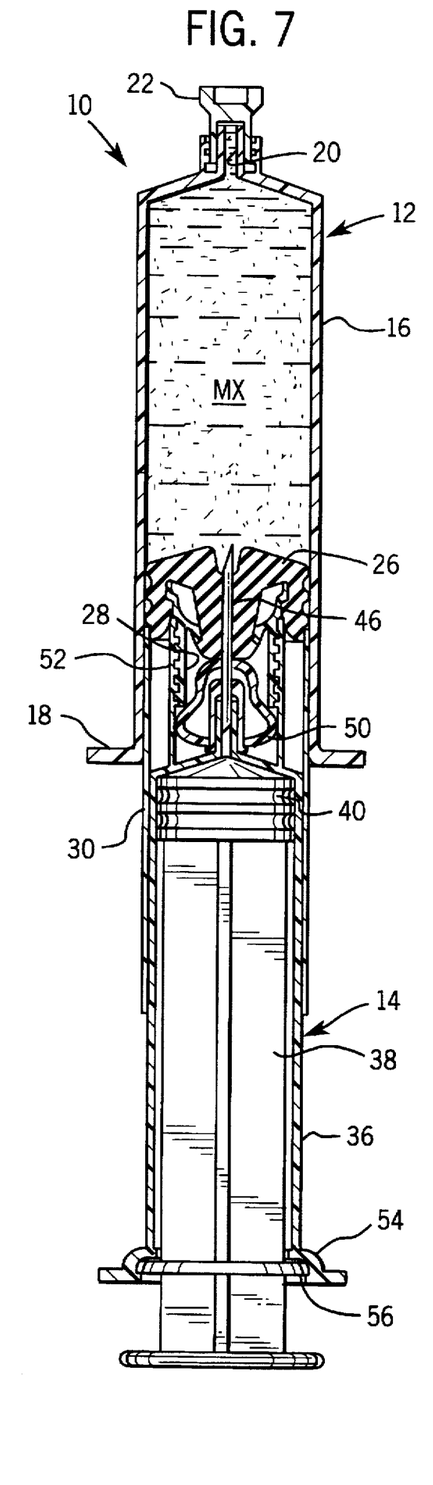
FIG. 7 is a cross-sectional view further illustrating the first embodiment after mixture of the drug concentrate with the liquid diluent.

By comparison of FIGS. 6 and 7, the relative repositioning of the various components of the drug delivery system will be observed. As movable piston plunger 38 is moved into the second syringe barrel 36, the liquid diluent D flows through the fluid discharge passage 42, through the cannula 46, and into the expandable mixing chamber 24 defined by the reciprocable stopper 26 and the first syringe barrel 16 of the first syringe assembly 12. As the diluent D and drug concentrate M are mixed, the resultant solution, designated as mixture MX in FIG. 7, is formed in the mixing chamber 24. As will be observed, flow of liquid from the second syringe assembly 14 into the mixing chamber 24 of the first syringe assembly 12 acts to move the reciprocable stopper 26, the sterility maintenance sleeve 30, and the second syringe assembly 14 outwardly (i.e. rearward or away from the drug delivery passage 20) in the first syringe barrel 16. The second syringe barrel 36 of the second syringe assembly 14 remains attached to, or fixed with respect to, the reciprocable stopper 26, as does the cannula 46 mounted on the second syringe assembly 14.

After the piston plunger 38 has been fully inserted into the second syringe barrel 36 of the second syringe assembly 14, the cooperating locking recess 54 and locking flange 56 move into locking engagement, thereby fixing the movable piston plunger 38 against further movement relative to the second syringe barrel 36. The drug delivery system appears as illustrated in FIG. 7, and is now ready for administration of the mixture MX which has been formed.

Figure 8:
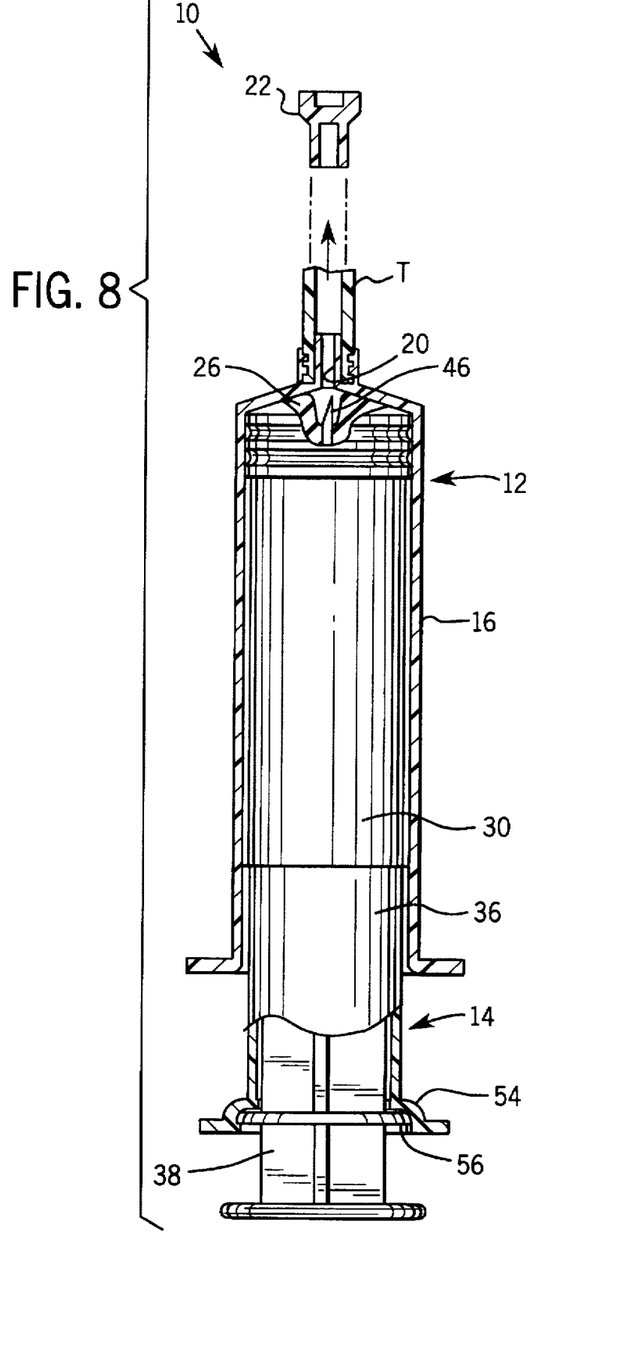
FIG. 8 is a further cross-sectional view illustrating the first embodiment after administration of the drug mixture.

Use of the present system for solution administration is generally illustrated in FIG. 8. After removal of cap 22, the drug delivery passage 20 of the first syringe barrel 16 of the first syringe assembly 12 is connected in fluid communication with a suitable connector or tubing T or other suitable administration means. The second syringe assembly 14 is then pushed or urged inwardly in the first syringe barrel 16 of the first syringe assembly 12. By this action, the second syringe assembly 14, the reciprocable stopper 26, and the sterility maintenance sleeve 30 move in unison inwardly (i.e. forward or toward the drug delivery passage 20 ) in the first syringe barrel 16, thereby causing the mixture MX to flow through the delivery passage 20. Administration of the mixture is thus complete, and the components of the system are ready for disposal.

Another embodiment of the invention, in a presently preferred form, is illustrated in FIGS. 9–16. Like the above-described first embodiment, the preferred second embodiment is a syringe system for accommodating a concentrated liquid or dry drug, by storing the concentrated drug and a liquid diluent separately, combining the concentrated drug and diluent to reconstitute the drug in solution form, and administering the mixed solution.

Figure 9:
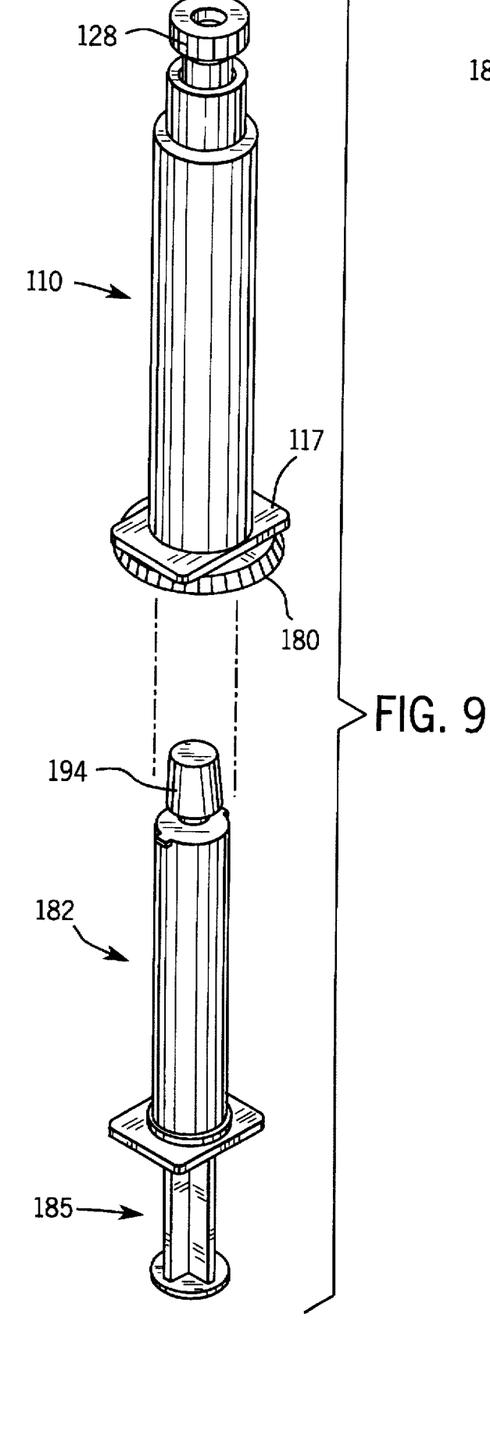
FIG. 9 is a perspective view illustrating the first syringe assembly and the second syringe assembly of the drug delivery system embodying the principles of a presently preferred, second embodiment of the invention.
Figure 10:
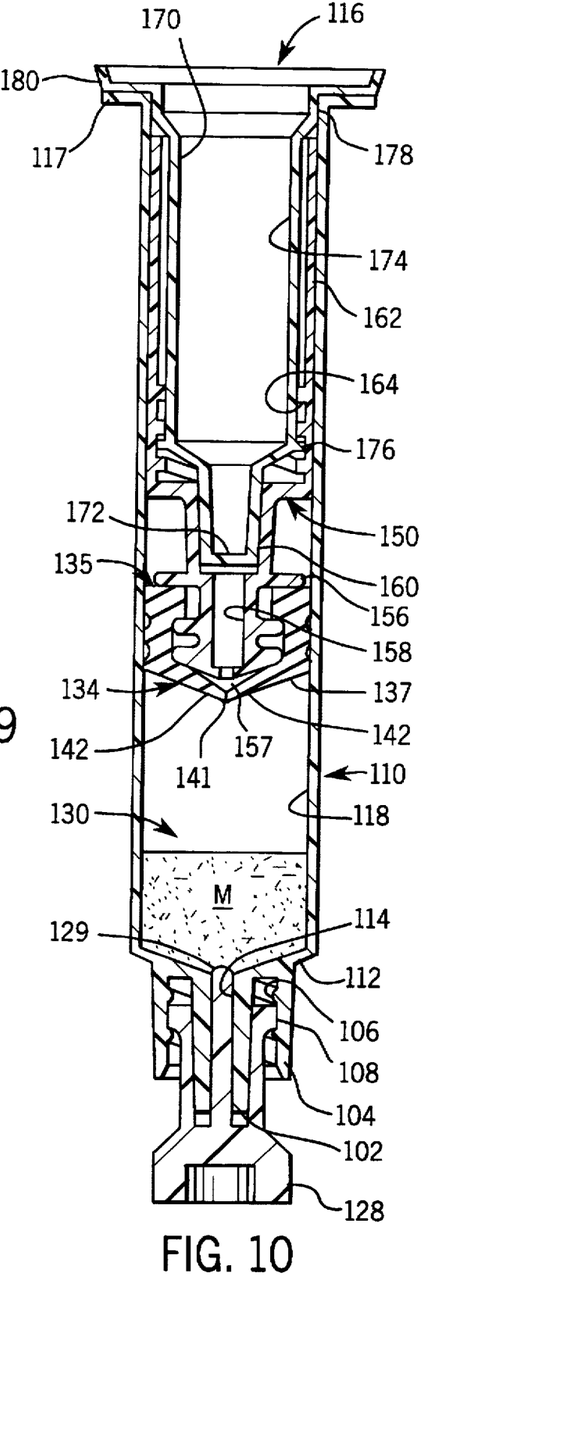
FIG. 10 is a cross-sectional view of a first syringe assembly of the second preferred embodiment shown in FIG. 9, and shows the first syringe assembly pre-filled with a drug concentrate designated M and sealed with a reciprocable stopper to which is mounted a sterility maintenance sleeve and a plug.

The system as seen in FIGS. 9 and 10 includes a first syringe assembly having a first syringe barrel 110. The first syringe barrel 110 includes a substantially closed end 112 which defines a delivery passage 114. The delivery passage preferably includes a male luer connection nozzle 102 surrounded by an annular collar 104 having an interior, female thread 106.

The delivery passage 114 is preferably closed with a removable closure 128 which has an internal stem 129 for occluding the delivery passage 114. The removable closure 128 also preferably includes an exterior lug or flange 108 for threadingly engaging the female thread 106 on the annular collar 104 at the delivery end of the first syringe barrel 110.

The first syringe barrel 110 has an open end 116 with a transverse flange 117. The first syringe barrel 110 is preferably cylindrical and preferably has a cylindrical interior surface 118.

When the removable closure 128 is properly secured to the first syringe barrel 110, the first syringe barrel 110 functions as a container defining an expandable mixing chamber 130 which can be filled with a predetermined quantity of a drug concentrate M which may be in a liquid or powder form. The concentrated drug M could be a lyophilized drug, for example.

A reciprocable stopper 134 is disposed within the first syringe barrel 110 at a first position to slidably seal and define the mixing chamber 130. The reciprocable stopper 134 may also be described as a grommet or slidable seal, and these terms may be used interchangeably.

The reciprocable stopper 134 has an outer side 135 facing the open end 116 of the first syringe barrel 110. The reciprocable stopper 134 also has an inner side 137 facing the delivery passage 114 of the first syringe barrel 110.

Figure 16:
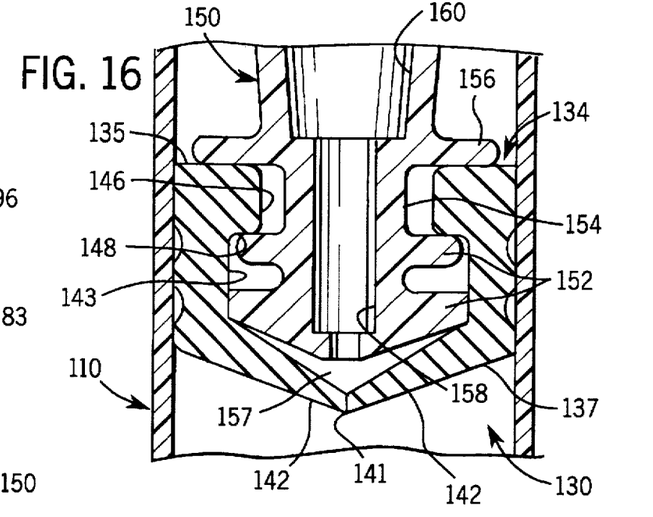
FIG. 16 is an enlarged, fragmentary, cross-sectional view illustrating structural details of the reciprocable stopper and the supporting structure of the sterility maintenance sleeve.

As best illustrated in FIG. 16, the reciprocable stopper 134 is resilient and has a generally hollow central portion. The reciprocable stopper 134 has at least one longitudinal slit 141 through the body of the reciprocable stopper. The slit defines flaps or lips 142 which are biased to a normally closed position. When pressurized from the outer side 135 of the reciprocable stopper, the lips 142 can open at the inner side 137 of the reciprocable stopper toward the delivery passage 114 of the first syringe barrel. Preferably, the inner side 137 of the reciprocable stopper defines a generally conical surface when the slit 141 is closed.

The reciprocable stopper 134 has an enlarged receiving cavity 143 defined in the hollow central portion adjacent the lips 142 of the reciprocable stopper The reciprocable stopper 134 also has a smaller entrance passage 146 between the outer side 136 of the reciprocable stopper and the enlarged receiving cavity 143 so as to define a retention shoulder 148 around the smaller entrance passage 146.

With continued reference to FIG. 16, the reciprocable stopper 134 is adapted to be mounted to the end of a sterility maintenance sleeve 150. The sterility maintenance sleeve 150 has an outlet end having an enlarged head 152 which is force-fit into the enlarged receiving cavity 143 of the resilient reciprocable stopper 134. The sterility maintenance sleeve 150 includes a reduced diameter neck 154 which is received in the smaller entrance passage 146 of the reciprocable stopper 134. A support flange 156 projects radially outwardly from the top of the neck 154 of the sterility maintenance sleeve adjacent the outer side 135 of the reciprocable stopper. The support flange 156 functions as a support which keeps the reciprocable stopper 134 from collapsing or otherwise excessively deforming in a manner that would permit undesirable fluid leakage.

As illustrated in FIGS. 10 and 16, the reciprocable stopper 134 preferably defines a clearance chamber or clearance space 157 between the lips 142 of the reciprocable stopper and the outlet end (bottom distal surface) of the enlarged head 152 of the sterility maintenance sleeve. This clearance space insures that the resilient lips 142 will always be able to close tightly against each other, even in the absence of a pressure differential sufficient to open them as described in detail hereinafter.

The enlarged head 152 at the outlet end of the sterility maintenance sleeve 150 has an outlet passage 158 from which fluid can flow into the clearance space 157 between the enlarged head 152 of the sterility maintenance sleeve and the inside surface of the lips 142 of the reciprocable stopper 134. As illustrated in FIGS. 10 and 16, the upper end of the outlet passage 158 of the sterility maintenance sleeve communicates with the interior of a luer socket 160 which projects upwardly above the support flange 156 of the sterility maintenance sleeve. The luer socket 160 is adapted to receive a luer nozzle of a diluent syringe as explained in detail hereinafter.

With continued reference to FIG. 10, the sterility maintenance sleeve 150 has an enlarged diameter body portion 162 having an interior female thread 164. As illustrated in FIG. 10, a removable plug 170 is provided for being initially inserted into the interior of the body portion 162 of the sterility maintenance sleeve 150. The plug 170 includes a nozzle-shaped distal end 172 for being received in the luer socket 160 of the sterility maintenance sleeve 150. The distal end 172 of the plug 170 is closed. however, so that there is no fluid passage from the plug 170 into the outlet passage 158 of the sterility maintenance sleeve.

The plug 170 also includes a cylindrical body portion 174 which has, at its lower end, a lug or engaging member 176 for threadingly engaging the interior, female thread 164 on the body portion 162 of the sterility maintenance sleeve 150. The upper end of the plug 170 includes an exterior seal ring or seal portion 178 for sealing the offset portion 121 of the interior surface 118 of the first syringe barrel 110 as described in detail hereinafter.

The plug 170 also includes a graspable portion 180. Preferably, the graspable portion 180 has an enlarged cross section and has an exterior surface which can be easily grasped to rotate the plug 170 to unthread it from the sterility maintenance sleeve 150 as described in detail hereinafter.

Figure 11:
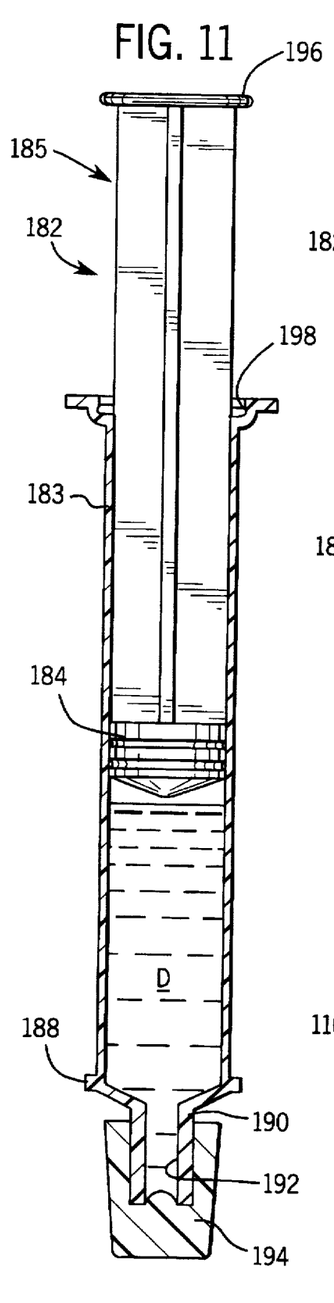
FIG. 11 is a cross-sectional view illustrating a second syringe assembly of the preferred embodiment, which second syringe assembly is pre-filled with a liquid diluent D for use with the first syringe assembly shown in FIG. 10.

The preferred embodiment of the syringe mixing system also includes a diluent syringe 182 as illustrated in FIG. 11. The diluent syringe 182 includes a diluent syringe barrel 183 that holds a liquid diluent D. The lower portion of the diluent syringe barrel 183 has an exterior engaging member or lug 188 for engaging the interior thread 164 of the sterility maintenance sleeve as described in detail hereinafter. The diluent syringe barrel 183 has a discharge end 190 in the form of a luer nozzle defining a discharge passage 192. Preferably, a removable exterior closure 194 is provided for sealingly closing the discharge passage 192 of the diluent syringe. The removable closure 194 may employ a friction fit, or alternatively, a snap-fit or threaded connection may be employed.

The diluent syringe 182 also includes a plunger assembly including a movable piston 184 and a plunger stem 185. The movable piston 184 is slidably and sealingly disposed in the diluent syringe barrel 183 and is used for expressing the liquid diluent D out of the syringe barrel 183 through the discharge passage 192 in the well known manner.

The preferred embodiment of the syringe system illustrated in FIG. 9 may be provided to the user as one package of two separate subassemblies. One subassembly is the prefilled and capped diluent syringe 182 as illustrated in FIG. 11. and the other subassembly includes the remaining components fitted together as illustrated in FIG. 10 with a drug M (which may be a lyophilized drug) in the first syringe barrel 110.

Alternatively the drug subassembly illustrated in FIG. 10 can be provided to the user in a separate single package. The diluent syringe 182 illustrated in FIG. 11 can also be supplied separately and stored for later use. At the time of use, the plug 170 is removed from the inside of the sterility maintenance sleeve 150 of the first syringe barrel 110 by rotating the plug in the clockwise or counterclockwise direction to unthread the plug 170 from the sterility maintenance sleeve 150. Preferably, the graspable portion 180 of the plug 170 has a knurled surface to accommodate the grasping of the plug between a person's thumb and fingers.

Figure 12:
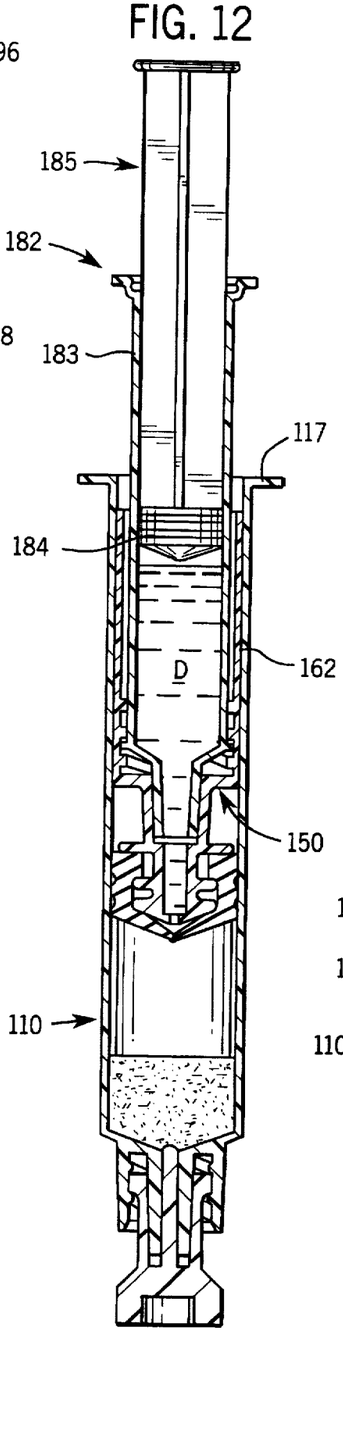
FIG. 12 is a cross-sectional view of the preferred embodiment of the components shown in FIG. 9 with the plug removed and the second syringe assembly telescopically inserted into the sterility maintenance sleeve in the first syringe assembly.

Next, the diluent syringe 182 (FIG. 11) is prepared for insertion into the sterility maintenance sleeve 150 of the first syringe barrel 110. The diluent syringe 182 can be inverted and the cap 194 removed. The first syringe barrel 110 can also be inverted and aligned with the inverted diluent syringe barrel 183. Relative longitudinal movement can then be effected so as to telescopically insert the diluent syringe barrel 183 into the sterility maintenance sleeve 150 in the first syringe barrel 110. The lug 188 on the diluent syringe barrel 183 is threadingly engaged with the female thread form 164 of the sterility maintenance sleeve as shown in FIG. 12. The diluent syringe barrel 183 is then threaded into the sterility maintenance sleeve 150 until the syringe barrel reaches the fully threaded position illustrated in FIG. 12.

Figure 13:
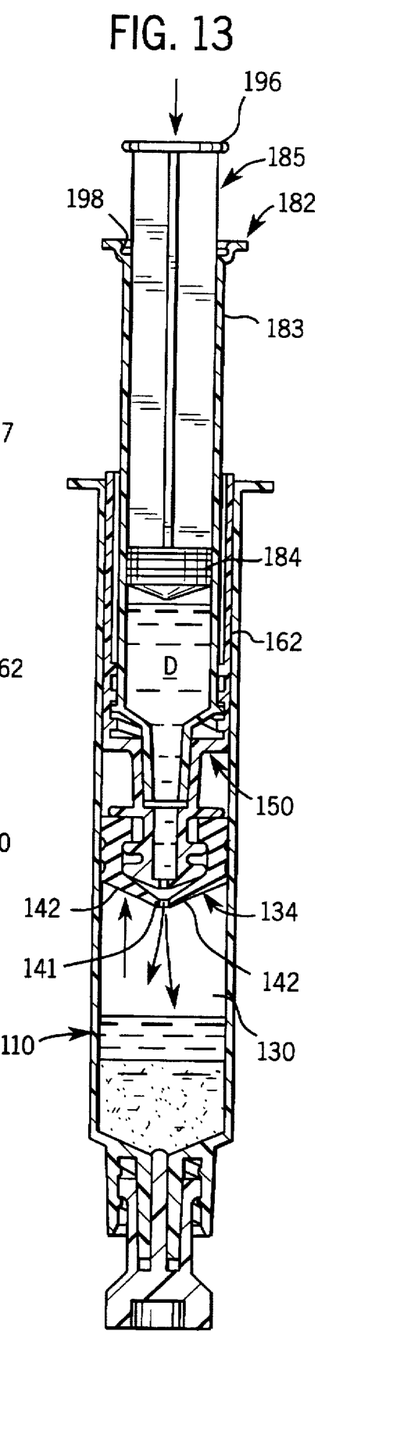
FIG. 13 is a cross-sectional view of the preferred embodiment similar to FIG. 12 and illustrates the advancement of the movable piston plunger of the second syringe assembly to establish fluid communication between the fluid chamber of the second syringe assembly and the mixing chamber of the first syringe assembly to cause fluid transfer of the liquid diluent D from the fluid chamber to the mixing chamber.

Referring now to FIG. 13. the liquid diluent D in the diluent syringe barrel 183 is expressed into the mixing chamber 130 of the first syringe barrel 110 by pushing on the plunger stem 185 of the diluent syringe.

Figure 14:
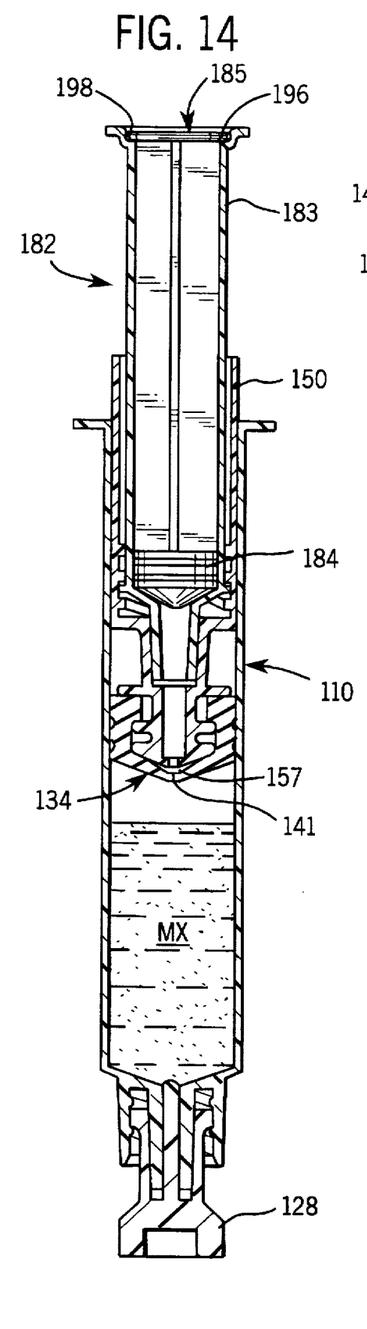
FIG. 14 is a cross-sectional view, similar to FIG. 13, further illustrating the preferred embodiment after mixture of the drug concentrate with the liquid diluent.

The slit 141 in the reciprocable stopper 134 opens under the increased pressure resulting from the movement of the movable piston 184. The liquid diluent D is thus forced into the first mixing chamber 130 of the first syringe barrel as shown in FIGS. 13 and 14. The liquid diluent D is thereby mixed or combined with the drug M. It the drug M is a dry powder such as a lyophilized drug, the liquid diluent D will reconstitute the drug in solution form. As the liquid diluent D fills the mixing chamber 130 in the first syringe barrel 110, the volume of the mixing chamber 130 increases, and the reciprocable stopper 134 is forced to slide outwardly in the first syringe barrel. As the reciprocable stopper 134 slides outwardly, the sterility maintenance sleeve 150 and the diluent syringe assembly 182 move outwardly with the reciprocable stopper 134.

The sterility maintenance sleeve 150 maintains the sterility of the interior surface 118 of the first syringe barrel 110 before and during the outward movement of the reciprocable stopper 134. Thus when the diluent is discharged from the second syringe barrel 183 into the mixing chamber 130 of the first syringe barrel, the expanding portion of the mixing chamber 130 has not been exposed to touch contamination. Thus the drug M and the diluent D are mixing in a sterile mixing chamber.

When all of the liquid diluent D has been expressed from the diluent syringe 182, the movable piston plunger 184 bottoms out in the diluent syringe barrel 183. Preferably, the upper, distal end of the plunger stem 185 has a radial flange 196, and the upper, distal end of the diluent syringe barrel 183 has a snap-fit type groove 198 for receiving and holding the radial flange 196 in a snap-fit engagement. The snap fit of the flange 196 and groove 198 retains the movable piston 184, the plunger stem 185 and the second syringe barrel 183 in a snapped-together condition. The snap fit prevents the movable piston 184 from being drawn outwardly from the diluent syringe barrel 183.

The snapped-together diluent syringe 182 together with the sterility maintenance sleeve 150 and the reciprocable stopper 134 can now function as the plunger and piston, respectively, of the primary administration syringe. In order to dispense the reconstituted drug solution MX, the assembled system shown in FIG. 14 can first be shaken to insure good mixing and then inverted.

Figure 15:
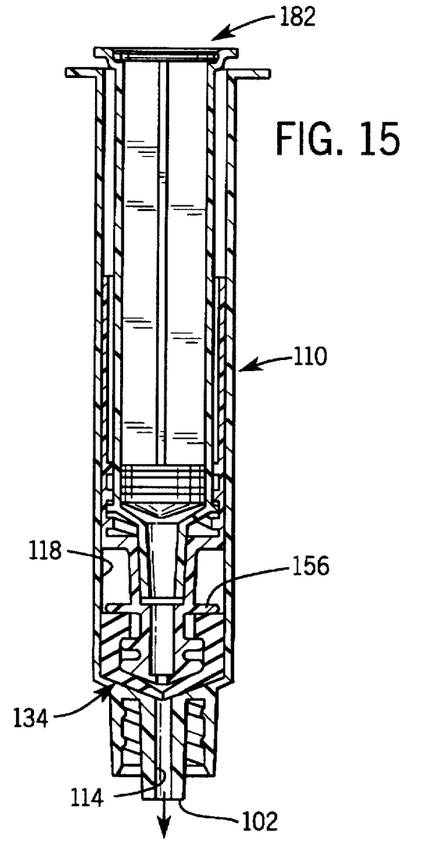
FIG. 15 is a further cross-sectional view illustrating use of the preferred embodiment of the drug delivery system shown in FIG. 14 for delivery and administration of the drug mixture.

The closure 128 is then removed from the inverted assembly. The snapped together and assembled plunger stem 185 and diluent syringe barrel 183 in conjunction with the reciprocable stopper 134 are then pushed to remove air from (i.e. prime ) the first syringe barrel 110 through the nozzle 102. The nozzle 102 may then be connected to an appropriate connector of an administration set or other conduit. Then the snapped together diluent syringe assembly 182 and the reciprocable stopper 134 are pushed further inwardly to express the drug solution MX out of the first syringe barrel 110 (FIG. 15). The hydraulic pressure of the drug solution in the first syringe barrel 110 forces the slit 141 in the reciprocable stopper to close (if it has not already closed) and to remain closed. The support flange 156 on the sterility maintenance sleeve 150 prevents undue deformation of the reciprocable stopper 134. The flange thus prevents leakage around the reciprocable stopper 134 between the reciprocable stopper 134 and the interior surface 118 of the first syringe barrel 110. Furthermore, the clearance space 157 between the enlarged head 152 at the lower end of the sterility maintenance sleeve 150 and the inside surface of the lips 142 of the reciprocable stopper permits the lips 142 on each side of the slit 141 to fully close.

In an alternative operation of the drug delivery system of the present invention, it will be appreciated that in all of the illustrated embodiments, the diluent D from the second syringe assembly 182 can be caused to flow into the first syringe barrel 110 from the second syringe barrel by pulling the two barrels (i.e. first barrel 110 and second barrel 183 in FIG. 13 for example) outwardly relative to each other. This will create a pressure differential as the mixing chamber 130 expands, which will move (i.e. pull or draw ) the diluent D in the second syringe barrel into the mixing chamber 130 of the first syringe barrel.

From the foregoing, it will be observed that numerous modifications and variations can be effected without departing from the true spirit and scope of the novel concept of the present invention. It is to be understood that no limitation with respect to the specific embodiments of the present disclosure herein is intended or should be inferred. The disclosure is intended to cover, by the appended claims, all such modifications as fall within the scope of the claims.

What is claimed is:

1. A drug delivery system, comprising:

a first pre-filled syringe assembly comprising:
  a first syringe barrel having an interior surface, an open end, and an opposite delivery end which defines a drug delivery passage;
  a reciprocable stopper slidably disposed within said first syringe barrel in sealing engagement therewith for defining an internal mixing chamber within said first syringe barrel in communication with said delivery passage; and
  a sterility maintenance sleeve extending from said reciprocable stopper toward said open end of said first syringe barrel, said sterility maintenance sleeve maintaining the sterility of the interior surface of said first syringe barrel;

a second pre-filled syringe assembly comprising
  a second syringe barrel having a fluid discharge passage at one end thereof, said second syringe barrel being sized to be disposed within the sterility maintenance sleeve of said first syringe assembly
  a movable piston plunger positionable within said second syringe barrel to define a fluid chamber therewith in communication with said fluid discharge passage; and
  a liquid in the fluid chamber of said second syringe barrel; and said system further including fluid transfer connector means for providing fluid communication from the fluid chamber of said second syringe assembly to said internal mixing chamber of said first syringe assembly when said second syringe assembly is disposed within said sterility maintenance sleeve so that the liquid within said fluid chamber can be caused to flow through said fluid transfer connector means into said internal mixing chamber of said first syringe assembly by movement of said piston plunger toward said fluid discharge passage of said second syringe assembly and thereafter caused to flow from said mixing chamber of said first syringe assembly through said drug delivery passage by movement of said second syringe assembly together with said reciprocable stopper and said sterility maintenance sleeve toward the drug delivery passage of said first syringe assembly, said fluid transfer connector means includes means for regulating the flow of fluid through said reciprocable stopper, said reciprocable stopper has an outer side facing toward said open end of said first syringe barrel and an inner side facing toward said drug delivery passage, said means for regulating the flow of fluid through said reciprocable stopper comprises said reciprocable stopper having a resilient body with a longitudinal slit through the resilient body defining two normally closed resilient lips, and the resilient body of said reciprocable stopper is substantially hollow and includes an enlarged cavity and a smaller entrance passage; and said sterility maintenance sleeve further includes:
  an enlarged head for being received in said enlarged cavity un said enlarged cavity of said resilient body,
  a smaller neck for being received in said smaller entrance passage of said resilient body, and
  a radially extending support flange adjacent said smaller neck for axially supporting said reciprocable stopper outer side.

2. A drug delivery system in accordance with claim 1, wherein said fluid transfer connector means further includes a fluid passageway through said enlarged head, smaller neck, and radial support flange of said sterility maintenance sleeve.

3. A drug delivery system in accordance with claim 2 wherein
  said inner side of said reciprocable stopper defines a conical surface tapering to an apex and said longitudinal slit is at the apex; and
  a clearance space is defined between said enlarged head of the sterility maintenance sleeve and said longitudinal slit when said lips are closed.

4. A drug delivery system, comprising:

a first pre-filled syringe assembly comprising:

a first syringe barrel having an interior surface, an open end, and an opposite delivery end which defines a drug delivery passage;

a reciprocable stopper slidably disposed within said first syringe barrel in sealing engagement therewith for defining an internal mixing chamber within said first syringe barrel in communication with said delivery passage; and a sterility maintenance sleeve extending from said reciprocable stopper toward said open end of said first syringe barrel said sterility maintenance sleeve maintaining the sterility of the interior surface of said first syringe barrel;

a second pre-filled syringe assembly comprising
  a second syringe barrel having a fluid discharge passage at one end thereof, said second syringe barrel being sized to be disposed within the sterility maintenance sleeve of said first syringe assembly
  a movable piston plunger positionable within said second syringe barrel to define a fluid chamber therewith in communication with said fluid discharge passage; and
  a liquid in the fluid chamber of said second syringe barrel; and said system further including fluid transfer connector means for providing fluid communication from the fluid chamber of said second syringe assembly to said internal mixing chamber of said first syringe assembly when said second syringe assembly is disposed within said sterility maintenance sleeve so that the liquid within said fluid chamber can be caused to flow through said fluid transfer connector means into said internal mixing chamber of said first syringe assembly by movement of said piston plunger toward said fluid discharge passage of said second syringe assembly and thereafter caused to flow from said mixing chamber of said first syringe assembly through said drug delivery passage by movement of said second syringe assembly together with said reciprocable stopper and said sterility maintenance sleeve toward the drug delivery passage of said first syringe assembly, said fluid transfer connector means includes means for regulating the flow of fluid through said reciprocable stopper, said means for regulating the flow of fluid through said reciprocable stopper comprises a normally closed, pressure actuatable valve, and said second syringe assembly and said sterility maintenance sleeve define means for engaging which comprises:
   a luer nozzle at said fluid discharge passage of said second syringe assembly, and
   a cooperating luer socket in said sterility maintenance sleeve.

5. A drug delivery system in accordance with claim 4, wherein said means for engaging further includes
   means for threadable connection on said second syringe assembly, and
   cooperating means for threadable connection associated with the sterility maintenance sleeve of said first syringe assembly.

6. A drug delivery system in accordance with claim 5, wherein
   said threadable connection means extends radially from said second syringe barrel, and
   said cooperating threadable connection means is a thread form in said sterility maintenance sleeve.

7. A drug delivery system in accordance with claim 6, wherein said second syringe assembly further includes locking means for locking said movable piston plunger against movement in said second syringe barrel after movement of said piston plunger causes said liquid to flow from said fluid chamber into said internal mixing chamber of said first syringe assembly.

8. A syringe system comprising:
   a first syringe assembly including
      a first barrel having an interior surface, an open end, and a delivery end defining a delivery passage to accommodate the delivery of a fluid mixture from said first barrel;
      a reciprocable stopper slidably disposed in said first barrel and defining a mixing chamber between said delivery end of said first barrel and said reciprocable stopper;
      a sterility maintenance member connected to and extending from said reciprocable stopper toward said open end of said first syringe barrel, said sterility maintenance member maintaining the sterility of the interior surface of said first syringe barrel; and
      a first constituent in said mixing chamber;

a second syringe assembly including
      a second barrel that is sized to be disposed in said sterility maintenance member and that has a discharge end defining a discharge passage communicating through said discharge end to accommodate the discharge of fluid from said second barrel;
      a moveable piston plunger slidably disposed within said second barrel and defining a second chamber between said discharge end and said piston plunger; and
      a liquid second constituent in said second chamber; wherein said reciprocable stopper and sterility maintenance member are engageable to cooperatively define a coupling means accommodating the flow of said liquid second constituent from said second syringe barrel into said mixing chamber as said second syringe assembly, together with the engaged sterility maintenance sleeve and reciprocable stopper move outwardly relative to said mixing chamber, said coupling means includes means for controlling fluid flow from said second chamber into said first chamber, said fluid flow controlling means includes a one-way pressure actuatable valve biased to a normally closed position.

said reciprocable stopper is made of a resilient material and has an inner side which conically tapers to an apex toward said first chamber and includes a reduced thickness portion at the apex of the conical shape with at least one slit through the apex into the first chamber to define said one-way pressure actuatable valve, said at least one slit defines opposed lips in said reciprocable stopper which are caused to resiliently open into said first chamber by fluid pressure from said second chamber, said reciprocable stopper further includes an outer side facing toward said first syringe barrel open end, said reciprocable stopper having an enlarged receiving cavity and a smaller entrace passage extending from said outer side to said enlarged cavity whereby the opening of said lips establishes communication from said enlarged cavity through said reciprocable stopper into said first chamber and whereby said lips are normally biased to a closed position, said sterility maintenance member includes a generally cylindrical sleeve; and said coupling means further includes a support structure on said sterility maintenance member, said support structure including an enlarged head and an adjacent smaller neck, said enlarged head being sealingly engaged with said enlarged receiving cavity of said reciprocable stopper and said smaller neck extending through said entrance passage of said reciprocable stopper, said sterility maintenance sleeve suport structure defining a central passageway through said enlarged head and smaller neck whereby said central passageway is normally occluded by said closed lips.

9. The syringe system in accordance with claim 8 wherein said sterility maintenance sleeve support structure further comprises a radial flange adjacent said smaller neck for axially supporting said outer side of said reciprocable stopper.

10. The syringe system in accordance with claim 9 wherein said coupling means further includes:
   a male luer nozzle disposed at said discharge end of said second barrel in fluid communication with said discharge passage; and a female luer socket in fluid communication with said central passageway through said sterility maintenance sleeve support structure, said male luer nozzle being insertable into said female luer socket as said second barrel is disposed within the sterility maintenance sleeve of the first barrel so that said one-way valve controls fluid flow between said second chamber and said first chamber.

11. The syringe system in accordance with claim 9 wherein said sterility maintenance sleeve support structure further includes engaging means; and said second syringe barrel further includes cooperating engaging means so that said second barrel is engageable with said sterility maintenance sleeve support structure on said reciprocable stopper.

12. The syringe system in accordance with claim 11 wherein said engaging means comprise a thread form on said sterility maintenance sleeve support structure; and said cooperating engaging means comprise a threadable flange on said second syringe barrel discharge end for threadingly engaging said sterility maintenance sleeve support structure thread form whereby a fluid tight connection is established between said discharge end of said second syringe barrel and said first syringe assembly.

13. The syringe system in accordance with claim 8, further including a first removable closure occluding said first barrel delivery passage;

a second removable closure occluding said second barrel discharge passage; and a cover removably mounted to said first barrel opposite said delivery end.

14. The syringe system in accordance with claim 8 wherein said reciprocable stopper is a resilient elastomeric material.

15. The syringe system in accordance with claim 8 further including a plug for sealing said open end of said first barrel outwardly of said sterility maintenance member.

* * * * *

UNITED STATES PATENT AND TRADEMARK OFFICE
CERTIFICATE OF CORRECTION

PATENT NO. : 5,785,682
DATED : July 28, 1998
INVENTOR(S) : Grabenkort

It is certified that error appears in the above-identified patent and that said Letters Patent is hereby corrected as shown below:

<u>ON THE TITLE PAGE:</u>

Item [75] Inventor section, change "Richard E." to --Richard W.--.

Signed and Sealed this

Twenty-third Day of February, 1999

Attest:

Q. TODD DICKINSON

Attesting Officer

Acting Commissioner of Patents and Trademarks